United States Patent [19]
Shultz

[11] Patent Number: 6,132,399
[45] Date of Patent: Oct. 17, 2000

[54] CATHETER SECUREMENT DRESSING AND DELIVERY METHOD

[75] Inventor: Tod H. Shultz, Arlington, Tex.

[73] Assignee: Kimberly-Clark Worldwide, Inc., Roswell, Ga.

[21] Appl. No.: 09/070,089

[22] Filed: Apr. 30, 1998

[51] Int. Cl.[7] .................................................. A61M 5/32
[52] U.S. Cl. .......................................... 604/174; 604/180
[58] Field of Search ................................... 604/174, 177, 604/179, 180, 523; 128/DIG. 26

[56] References Cited

U.S. PATENT DOCUMENTS

| | | |
|---|---|---|
| D. 385,038 | 10/1997 | Shultz . |
| 3,918,446 | 11/1975 | Buttaravoli . |
| 3,967,621 | 7/1976 | Schwarz . |
| 3,995,629 | 12/1976 | Patel . |
| 4,096,863 | 6/1978 | Kaplan et al. . |
| 4,165,748 | 8/1979 | Johnson . |
| 4,275,721 | 6/1981 | Olson . |
| 4,571,245 | 2/1986 | Hubbard et al. . |
| 4,583,976 | 4/1986 | Fergeson . |
| 4,614,183 | 9/1986 | McCracken et al. . |
| 4,617,017 | 10/1986 | Hubbard et al. . |
| 4,622,034 | 11/1986 | Shattuck . |
| 4,641,643 | 2/1987 | Greer . |
| 4,669,458 | 6/1987 | Abraham et al. . |
| 4,678,462 | 7/1987 | Vaillancourt . |
| 4,704,177 | 11/1987 | Vaillancourt . |
| 4,799,926 | 1/1989 | Haber . |
| 4,838,868 | 6/1989 | Forgar et al. . |
| 4,875,896 | 10/1989 | Kurtz . |
| 4,917,112 | 4/1990 | Kalt . |
| 4,976,700 | 12/1990 | Tollini . |
| 4,989,587 | 2/1991 | Mera . |
| 5,012,801 | 5/1991 | Feret . |
| 5,116,324 | 5/1992 | Brierley et al. . |
| 5,147,322 | 9/1992 | Bowen et al. . |
| 5,282,791 | 2/1994 | Lipton et al. . |
| 5,292,312 | 3/1994 | Delk et al. . |
| 5,300,037 | 4/1994 | Delk et al. . |
| 5,497,788 | 3/1996 | Inman et al. . |
| 5,630,430 | 5/1997 | Schultz et al. . |

FOREIGN PATENT DOCUMENTS

| | | |
|---|---|---|
| WO 9504511 | 2/1995 | WIPO . |
| WO 9810823 | 3/1998 | WIPO . |
| WO 9815312 | 4/1998 | WIPO . |

OTHER PUBLICATIONS

PCT International Search Report dated Aug. 5, 1999 for International Application No. PCT/US99/09298, filed Apr. 29, 1999.

U.S. application No. 08/858,015, Filed May 16, 1997, Entitled "Wound Covering Device".

U.S. application No. 09/050,720, Filed Mar. 30, 1998, Entitled "Wound Closure Device for Viewing a Wound and Method".

U.S. application No. 09/050,715, Filed Mar. 30, 1998, Entitled "Wound Closure Device".

*Primary Examiner*—Glenn K. Dawson
*Assistant Examiner*—Michael J. Hayes
*Attorney, Agent, or Firm*—Dority & Manning, P.A.

[57] ABSTRACT

A securement device is provided for securing a catheter to a patient's skin. An elongated handle member is used to align and apply the device to the patient's skin. A cover dressing is releasably attached to the handle member and has a covering side configured for placement against the patient's skin to cover at least the entry wound created by the catheter. The holder includes a securing member with a first side having an adhesive thereon for securing to the patient's skin adjacent to the point of entry of the catheter through the skin. The securing member includes an opening therethrough to allow a protrusion or portion of the catheter to extend therethrough while the first side of the securing member adheres the catheter to the patient's skin on opposite sides of the opening. The cover dressing is foldable over the securing member along a hinge section between the securing member and the cover dressing. Once the first side of the securing member is pressed over the catheter and against the patient's skin adjacent to the insertion point or wound site, the handle member is used to pull and fold the cover dressing at the hinge section so that the cover dressing folds over the securing member and covers the insertion wound through the patient's skin.

7 Claims, 4 Drawing Sheets

CATHETER SECUREMENT DRESSING AND DELIVERY METHOD

BACKGROUND OF THE INVENTION

The present invention relates generally to a device for securing medical devices to a patient's skin, and more particularly to an aseptic delivery catheter securement dressing for holding a catheter or IV to a patient.

Various medical devices are known that pierce or penetrate a patient's skin, for example, catheters and IV units. It is often necessary to secure the medical device near its insertion or entry point on the patient's body to ensure proper placement and functioning of the device, as well as to offer some degree of comfort and mobility for the patient. In addition, certain medical procedures require the application of a tensile force, known as traction, to the catheter or IV, thus making it particularly necessary to firmly secure the device in its longitudinal direction.

In addition, the insertion point of the medical device through the patient's skin essentially creates a wound that, in many instances, should be covered and treated as any other skin wound. Despite disinfection procedures, bacteria can remain on the patient's skin surface and can contaminate venous catheters upon or after insertion. Improvements in catheter design and delivery techniques are needed to prevent such contamination from occurring.

Conventionally, medical practitioners have used strips of medical-grade adhesive tape to secure the medical device directly to the patient's skin adjacent the insertion point. The wound is then separately covered by any conventional wound covering or bandage. This conventional method has significant drawbacks. The insertion point of the medical device is not visible and the wound covering must be removed each time the wound is checked. Additionally, the delivery technique is not aseptic and it is extremely difficult to maintain the wound in a clean environment and to prevent contamination of the wound site due to the relatively close proximity of the catheter. The conventional practice is time consuming, particularly wasteful of tape, bandages, etc., and may even add to wound contamination and infection.

Various types of catheter or other medical securing devices have been developed in the art. For example, U.S. Pat. Nos. 4,096,863; 4,571,245; and 4,617,017. Each disclose catheter securing devices comprising a strap which encircles the limb of the patient. U.S. Pat. Nos. 4,165,748 and 4,976,700 disclose a second type of catheter securing device comprising a segment of material having one side coated with adhesive which is designed to be applied directly to the patient's skin. A central tab extends from the segment of material and has fastening means for securing the catheter also. This type of device has no means for addressing the wound caused by the catheter or IV unit and functions properly only for particular sizes of the catheter tubes. U.S. Pat. No. 5,147,322 discloses a medical appliance securing device having an anchoring patch with one surface coated with an adhesive for attaching at any desired location on the patient's skin. A retaining tab extends from the anchoring patch with fastening means located on the free end of the retaining tab. Complimentary fastening means are located on the top surface of the anchoring patch. The design of the retaining tab allows the application of traction to the catheter and allows the device to restrain various diameters of catheter tubes or other tubular members.

OBJECTS AND SUMMARY OF THE INVENTION

A principle object of the present invention is to provide an improved method of delivery and securement for all types of catheters.

An additional object of the present invention is to provide a catheter securement device that significantly reduces the risk of contamination or infection at the wound site of the catheter.

Still a further object of the present invention is to provide an improved securement device having means for securing any manner of catheter or similar device at a point of insertion through the patient's skin while simultaneously providing for a wound covering or dressing that allows for visible inspection and monitoring of the wound site.

Additional objects and advantages of the invention will be set forth in part in the following description, or may be obvious from the description, or may be learned through practice of the invention.

In accordance with the objects and purposes of the invention, a securement device is provided for use where any manner of catheter or similar device is secured to a patient's skin and has a point of entry through the patient's skin. The catheter can comprise any conventional type of catheter or IV device used to introduce or withdraw fluids from a patient through an insertion wound in the patient's skin.

The securement device according to the invention includes an elongated handle member configured for aligning and applying the device to the patient's skin. A cover dressing is releasably attached to the handle member and has an entry point covering side configured to cover the entry point or insertion wound of the medical device through the skin. This entry point covering side of the cover dressing is held to the patient's skin, by, for example, an adhesive on the cover dressing.

The device includes a securing member with an end thereof attached to the cover dressing and a first side with an adhesive thereon for being adhered to the patient's skin adjacent to the point of entry of the catheter through the skin. The securing member may include an opening, recess, or the like, therethrough configured to allow a protrusion or other portion of the catheter to extend therethrough while the first side of the securing member adheres to the patient's skin and the catheter on opposite sides of the portion.

The cover dressing is foldable over the securing member along a hinge line or section. Once the first side of the securing member is pressed over the catheter and against the patient's skin adjacent to the point of entry of the catheter through the skin, a handle member is used to pull and fold the cover dressing at the hinge section or line so that the cover dressing folds over the securing member and covers the wound site.

In a preferred embodiment of the invention, different layers of adhesive may be applied to different sides of the various components. For example, an adhesive may be disposed on the entry point covering side of the cover dressing for adhering the cover dressing to the patient's skin. In this embodiment, the handle member is releasably secured to the adhesive on the cover dressing. Likewise, an adhesive may be provided on the second side of the securing member. The handle member is releasably secured to this adhesive on the second side of the medical device securing member and the cover dressing also adheres to this adhesive layer on the securing member.

The cover dressing is preferably formed of a transparent film material and is foldable along the hinge section or line. In a preferred embodiment, the hinge section is defined by overlying portions of the cover dressing and the securing member. The cover dressing is delivered aseptically to the wound site and creates an environment impervious to external contamination. The cover dressing preferably has a width relative to the securing member to ensure that the cover dressing completely covers the insertion wound adjacent to the point on the patient's skin where the securing member secures the catheter device to the skin. The cover dressing may also include and opening corresponding to the opening in the securing member. However, in a preferred embodiment, the cover dressing is a continuous member that also covers the opening in the securing member and thus, also, the portion of the medical device or catheter held by the securing member.

In a preferred embodiment of the invention, the securing member comprises longitudinally extending arms that define an opening therebetween. The arms are connected at their forward end and also at the opposite end generally adjacent to the hinge section of the holder. It should be appreciated, however, that the securing member can take on any configuration. For example, the securing member may comprise a single strip of any shape and need not include an opening or recess therein for accommodating the catheter or any portion thereof. The securing member may completely cover the catheter where it adheres the catheter to the patient's skin.

The present invention also provides a method for delivering and securing any manner of catheter device to a patient's skin wherein the device is also inserted through the patient's skin. The present inventive method provides an aseptic technique for delivering and securing catheters wherein the dressing is not exposed to air, assisting devices, or a care giver's hands thus significantly reducing the risk of contamination or infection from these sources. The method comprises attaching the securement device to the patient's skin adjacent the point of insertion of the device through the skin with an adhesive securing member. The securing member includes a cover dressing attached to an end thereof. The method then calls for folding the cover dressing back over the adhesive securing member and pressing the cover dressing against the medical device and the patient's skin with the use of a handle member wherein the care giver does not touch the wound covering side of the cover dressing.

Finally, the method includes covering the point of insertion of the medical device through the patient's skin with the folded over cover dressing to provide a clean and essentially sealed environment for the insertion wound.

In a preferred method according to the invention, the cover dressing is folded over the securing member along a hinge section or line generally at the connection location of the cover dressing with the securing member.

Preferably, the cover dressing has adhesive on the side thereof that covers the insertion wound. The method includes pressing the adhesive side of the cover dressing against the patient's skin and around the insertion wound.

The method also includes the inventive steps of applying the securement device in an aseptic manner with a handle member that is releasably attached to the adhesive on the cover dressing. The method includes simultaneously peeling the handle member from the cover dressing while using the handle member to fold the cover dressing back over the securing member so that the side of the cover dressing to be pressed against the patient's skin and over the insertion wound is not touched by the operator, the patient's skin, or any other assisting or medical devices, and is essentially not exposed to air prior to being applied to the patient's skin.

Preferably, the securement device according to the invention includes a protective member releasably attached to the adhesive on the securing member. As a first step, this protective member is removed from the securing member prior to securing the catheter to the patient's skin with the securing member.

It should be appreciated by those skilled in the art that the present invention has many applications in the medical industry. The invention is applicable wherever a medical device or any manner of catheter is to be held to the patient's skin and a portion or end of the medical device is inserted through the skin. The present invention also provides a relatively simple and easy aseptic method for delivering and securing a catheter to the skin while providing a system for maintaining the insertion wound in a clean state that is essentially impervious to outside contamination sources without the use of additional bandages, dressings, or additional procedures.

DETAILED DESCRIPTION OF THE PREFERRED EMBODIMENTS

Figure 1:
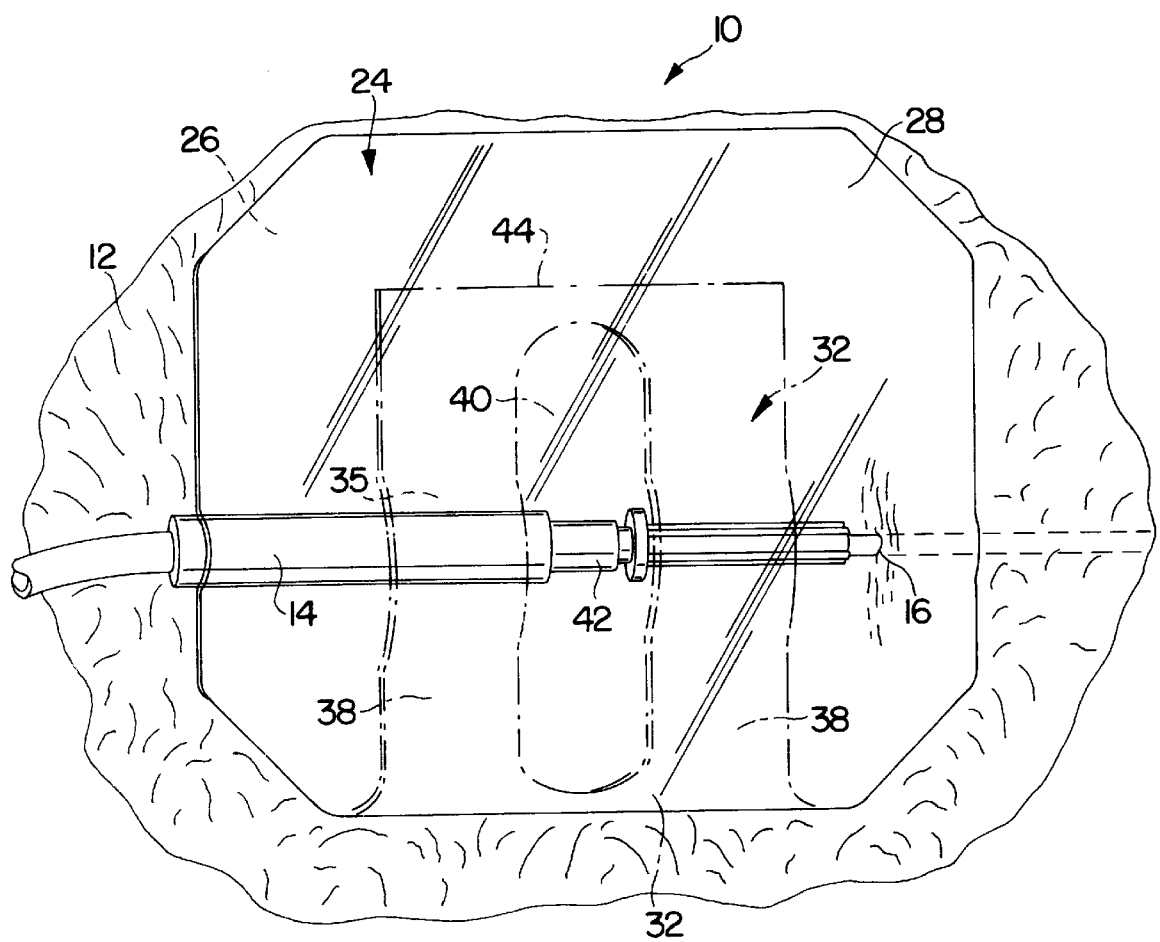
FIG. 1 is a perspective view of the securement device according to the invention as used to hold a catheter or IV device to a patient's skin adjacent to an insertion wound of the medical device through the skin.
Figure 2:
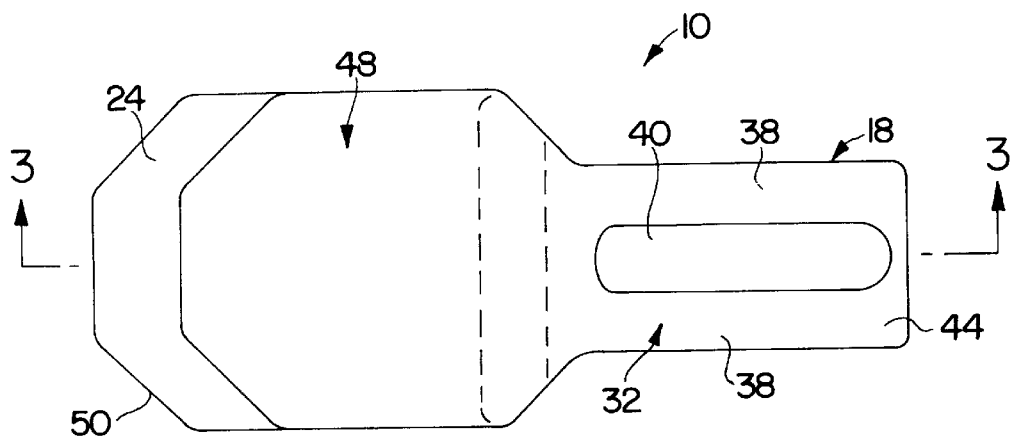
FIG. 2 is a top view of a securement device constructed in accordance with the present invention.

Reference will now be made in detail to the presently preferred embodiments of the device and method according to the present invention, one or more examples of which are illustrated in the drawings. Each example is provided for explanation of the invention and is not meant as a limitation of the invention. For example, features illustrated or described as part of one embodiment can be used with another embodiment to create still a third embodiment. It is intended that the present invention cover such modifications and variations as come with the scope and spirit of the invention.

Referring to the figures in general, a securement device 10 is illustrated. As described herein, device 10 can be used with any conventional catheter or IV type of medical device wherein the device enters a patient's skin at a point of entry causing an insertion wound and must also be held or secured to the patient's skin adjacent to the insertion wound. Though the medical device is illustrated in the figures as a conventional catheter, it should be appreciated that the present invention is not limited to use with only such a device.

The present invention is related in subject matter to the wound closure devices described in U.S. Pat. Nos. 5,497,788 and 5,630,430 commonly owned by the present assignee, Tecnol Medical Products, Inc., such patents being incorporated herein in their entirety for all purposes.

Referring generally to FIGS. 1 through 4, securement device holder 10 according to the invention includes an elongated handle member 18, which has a first side 20 and an opposite side 22. As will be explained in greater detail below, handle member 18 has an enlarged portion 50 and a narrower portion 51 extending therefrom. An opening 21 may be defined in the narrow portion 51 as particularly illustrated in FIG. 4. Opening 21 will be explained in greater detail below.

Device 10 also includes a cover dressing, generally 24. Cover dressing 24 has an wound site covering side 26 and an opposite side 28. Cover dressing 24 serves to cover and essentially seal at least the insertion wound where the medical device enters the patient's skin, and provides an environment for the wound essentially impervious to outside sources of contamination. Cover dressing 24 can comprise any shape or size and the configuration illustrated in the figures is merely an example of one preferred embodiment of cover dressing 24.

When disposed in an overlying relation to the insertion wound, as generally illustrated in FIG. 1, cover dressing 24 preferably forms a barrier around the insertion wound. This barrier prevents external contaminating sources from entering the wound site, and may also prevent wound exudates from leaking from the wound site. Cover dressing 24 may be transparent or opaque. Utilizing a transparent cover dressing is advantageous in that it facilitates observation and monitoring of the insertion wound. Cover dressing 24 may be formed from any variety of materials, including polyethylene, polyurethane, polypropylene, polyester, woven or non-woven substrates, a hydrogel, or any combination of such materials. Depending on the application, cover dressing 24 may comprise a hydrophobic material or a hydrophilic material to further assist the healing process. Cover dressing 24 may be loaded with one or more medicinal agents, such an antimicrobial compound, antifungal compound, vitamins, an antibiotic compound, or any combination of such agents. The medicinal agents may also be loaded in an adhesive deposited on the wound site covering side 26 of cover dressing 24.

Device 10 also includes a catheter securing member generally 32. Securing member 32 has a first side 35 and an opposite second side 39. First side 35 is the side configured to be pressed against the patient's skin for a medical device, such as catheter 14, to the skin 12 adjacent to the insertion point or wound site 16 of the catheter through the patient's skin. In this regard, first side 35 has an adhesive 36 disposed on at least a portion thereof.

Securing member 32 is connected or attached to cover dressing 24 generally at an end 34 thereof. In a preferred arrangement illustrated particularly in FIG. 3, securing member 32 is attached to cover dressing 28 along a hinge section or line, generally 46, wherein a portion 52 of securing member 32 overlies a portion 54 of cover dressing 24. In this regard, an adhesive 37 on second side 39 of securing member 32 adheres the securing member to cover dressing 28 at the overlying portions 52, 54. It should be appreciated, however, that the securing member and cover dressing can be attached or connected by any conventional means or arrangements. Furthermore, it should be understood that securing member 32 may also comprise an extension of the same material defining cover dressing 24.

Securing member 32 also includes a space, such as opening 40, generally defined therethrough that permits a portion or protrusion 42 of catheter 14 to extend through or beyond the securing member. An opening 40, or similar accommodating cut-out or recess, may be preferred in that it provides for a way to accommodate protruding shoulders or joints of the catheter without sacrificing the integrity of the securing member. In the embodiment illustrated, opening 40 is defined by longitudinally extending and spaced apart arm members 38 joined at a forward end 44. Arm members 38 are joined at the other end generally along hinge section 46. Referring in particular to FIG. 1, as is commonly understood, conventional catheter or IV medical devices 14 may include a number of components that are joined at junctions or shoulders, for example, protruding shoulder 42. Opening 40 has a shape and size to accommodate such junctures or shoulders while arm members 38 adhere to the medical device on opposite sides of the junction or protrusion 42 and the patient's skin. In this regard, the protrusion or junction 42 does not limit the adhesive surface area of securing member 32 and also provides for a means of easy visual inspection of the integrity of the junction point. It should be appreciated that opening 40 may have any shape or size and may be defined by any number of components of securing member 32. For example, opening 40 may be defined in a single extending arm member, or may be open at one end thereof. In an alternative embodiment, opening 40 may be defined by a space or area adjacent to an extending arm member, for example an off-center securing member 32, and need not be circumscribed by securing member 32.

Securing member 32 generally has a width equal to that of cover dressing 24 where the two components are joined along hinge section 46. Securing member 32 may then narrow towards end 44, as particularly illustrated in the figures. In this manner, securing member 32, for example one of arms 38, is used to secure medical device 14 directly adjacent to the entry or insertion wound 16 without covering or extending over the wound. Thus, the width of arms 38 is sized to hold the medical device adjacent to the wound without interfering with the entry point of the device through the skin.

Securing member 32 may be formed of any number of materials including polyethylene, polyurethane, polyester, woven substrates, non-woven substrates, hydrogel, foam, or any combination of such materials. For example, securing member 32 may actually be formed of the same material as cover dressing 24. To further assist in healing of the entry wound, securing member 32, or the adhesive deposited thereon, may also be loaded with one or more medicinal agents, such as an antimicrobial compound, antifungal compound, vitamins, and/or antibiotic compound.

In the embodiment of the invention illustrated in the figures, securing member 32 has an adhesive layer 36 disposed at least on parts of first surface 35 intended to adhere surface 35 to the patient's skin. A second adhesive layer 37 is disposed on opposite side 39 of securing member 32 and adheres overlying portion 52 of the securing member to overlying portion 54 of cover dressing 24, as discussed above. Adhesive layer 37 also releasably attaches handle member 18 to side 39 of securing member 32. The "adhesive" may also be an epithelial reactant that reacts with the upper layer of the patient's skin and essentially bonds thereto.

Thus, in the embodiment illustrated, three adhesive layers are used in the device. First adhesive layer 30 is disposed at least on sections of entry point covering side 26 of cover dressing 24. A second adhesive layer 36 is provided on first side 35 of securing member 32 to adhere the securing member to the medical device and to the patient's skin. A third adhesive layer 37 is disposed on at least portions of second side 39 of securing member 32 and releasably holds handle member 18 to securing member 32. It should be understood, however, that the use of conventional adhesives, although preferred, is not necessary to utilize the invention. For example, handle member 18 can be held to securing member 32 with non-adhesive means. For example, either handle member 18 or securing member 32 may comprise a material having an inherent tackiness or attraction to the other material. Likewise, either of the materials may be statically charged to hold the other material. In the same manner, adhesive 30 on cover dressing 24 may not be necessary to hold cover dressing 24 against the patient's skin. Cover dressing 24 may be formed of a material having an inherent ability to cling to the patient's skin without an additional adhesive. Cover dressing 24 may also be statically charged to adhere to the patient's skin. Any number of methods may be used to adhere the surfaces as discussed above.

Figure 3:
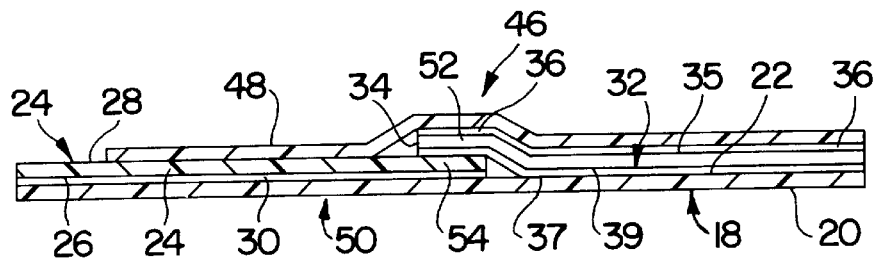
FIG. 3 is a sectional side view of the embodiment of the device illustrated in FIG. 1.
Figure 4:
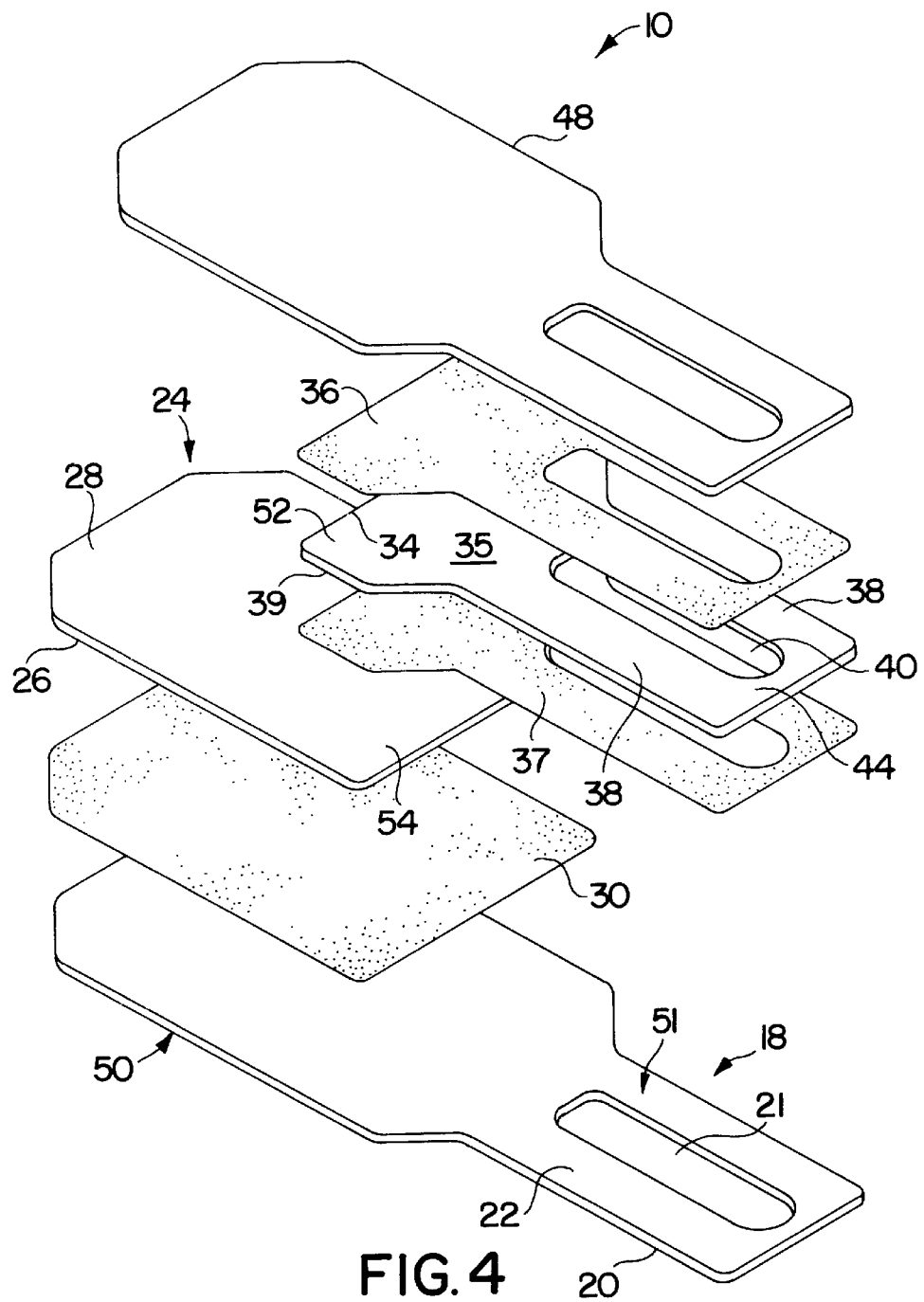
FIG. 4 is an exploded component view of the securement device according to the invention.

Securement device 10 according to the invention is illustrated in FIG. 3 as the product would be stored prior to use. Device 10 includes a protective member or membrane, generally 48, releasably attached to first side 35 of securing member 32 by adhesive layer 36. A release agent or coating may be applied to the side of protective member 48 adjacent to adhesive layer 36 so that protective member 48 can be easily separated from securing member 32. Protective member 48 is at least coextensive with adhesive layer 36 so as to prevent undesired exposure of adhesive layer 36 prior to application of securing member 32 to the patient's skin. Protective member 48 may be fashioned to have dimensions different from those of handle member 18 so that protective member 48 can be easily removed from securing member 32. Protective member 38 may be formed from any variety of materials including paper, polyester, polyethylene, or laminates of these materials.

To ensure that handle member 18 does not pull securing member 32 away from the patient's skin in application of device 10, it is preferable to ensure that an adhesive differential is maintained between handle member 18 and side 39 of securing member 32 as compared with the bond between side 35 of securing member 32 and the patient's skin. This can be ensured in any number of ways. For example, adhesive 37 between handle member 18 and side 39 may be weaker than adhesive 36. It is also possible that handle member 18 is attached to side 39 and/or side 26 without the use of an adhesive. In the case where adhesives 37 and 36 are essentially the same, it may be sufficient to ensure that the adhesive surface area between handle member 18 and side 39 is less than that of side 35 and the patient's skin.

The aseptic delivery of securement device 10 according to the invention will now be described with reference to sequential FIGS. 5a through 5d. Once the operator has peeled protective member 48 from side 35 of securing member 32, arms 38 are positioned on opposite sides of protrusion or junction 42 and side 35 is then pressed against the patient's skin and the medical device on opposite sides of junction 42 adjacent to insertion point or wound site 16 of the medical device through the skin, as particularly illustrated in FIG. 5. In this manner, arms 38 are adhered to the medical device and the patient's skin. The operator firmly presses the sections of securing member 32 having adhesive thereon against the patient's skin, including end 44.

Figure 5A:
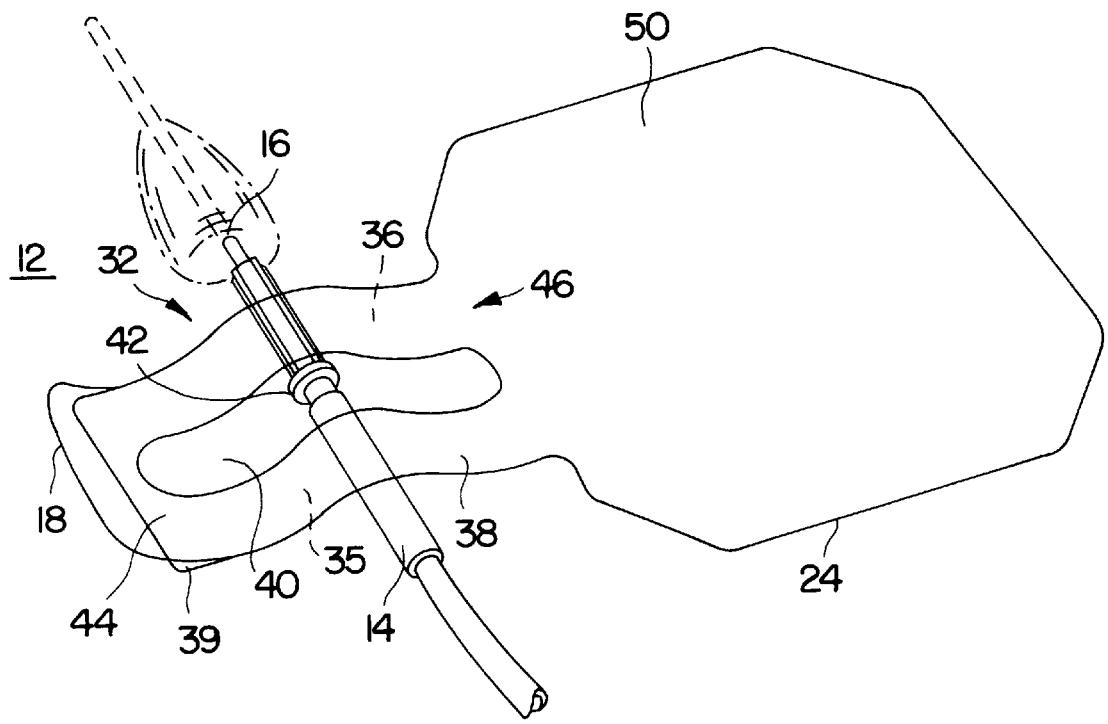
FIGS. 5a through 5d are sequential operational views of the securement device according to the invention.
Figure 5B:
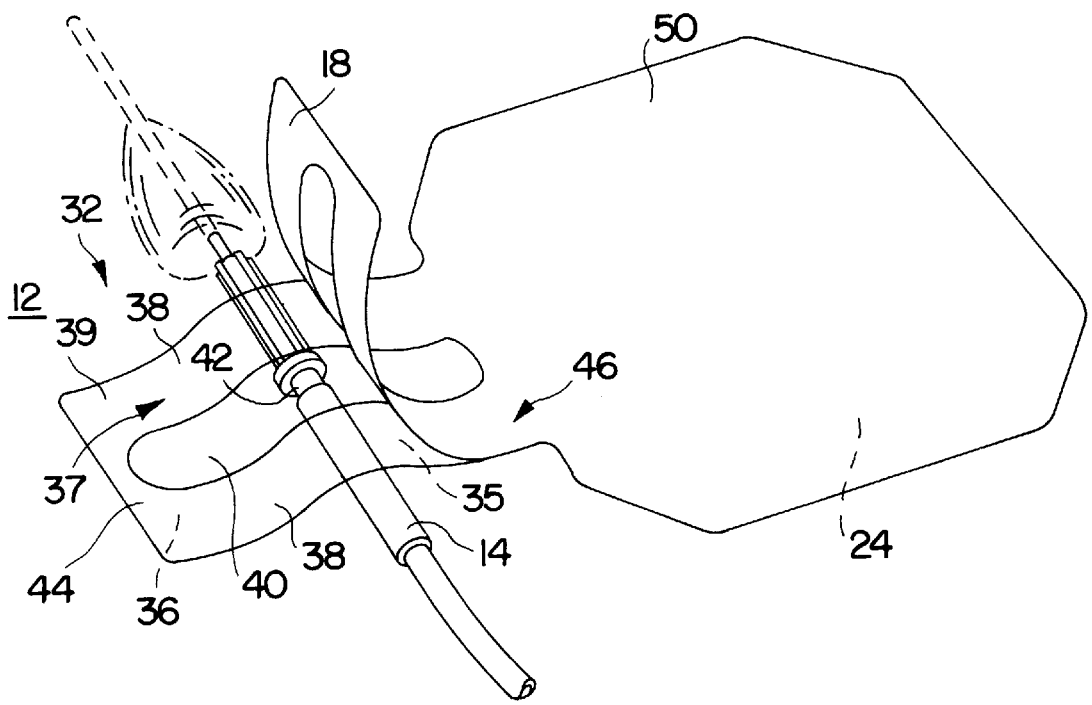
Figure 5C:
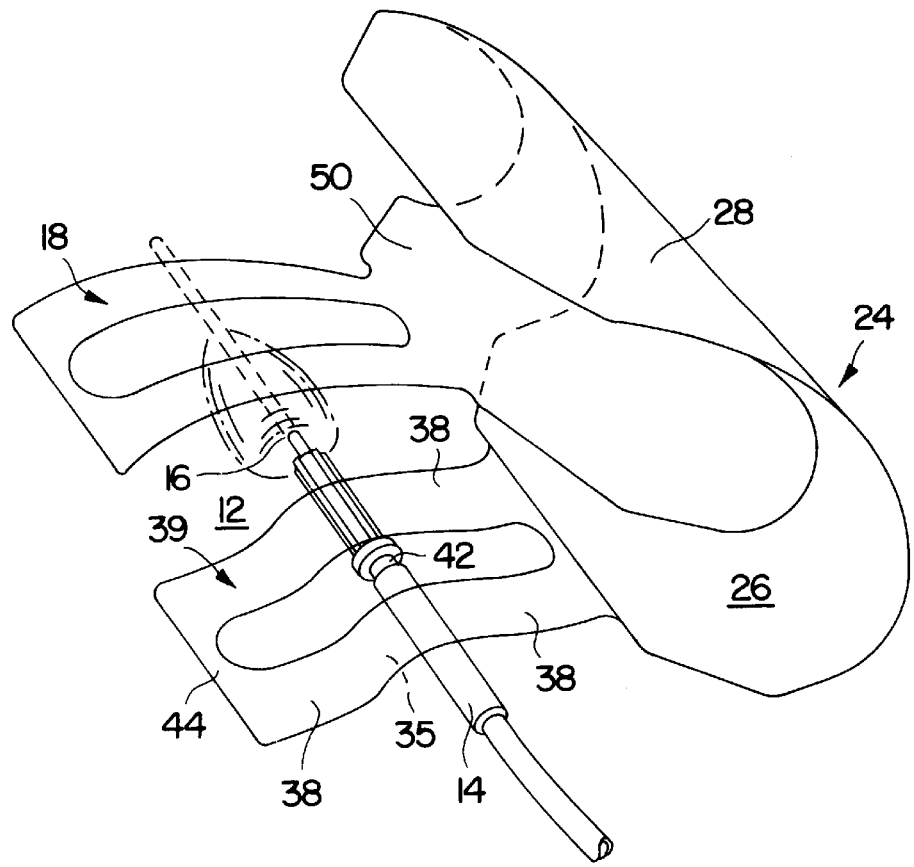
Figure 5D:
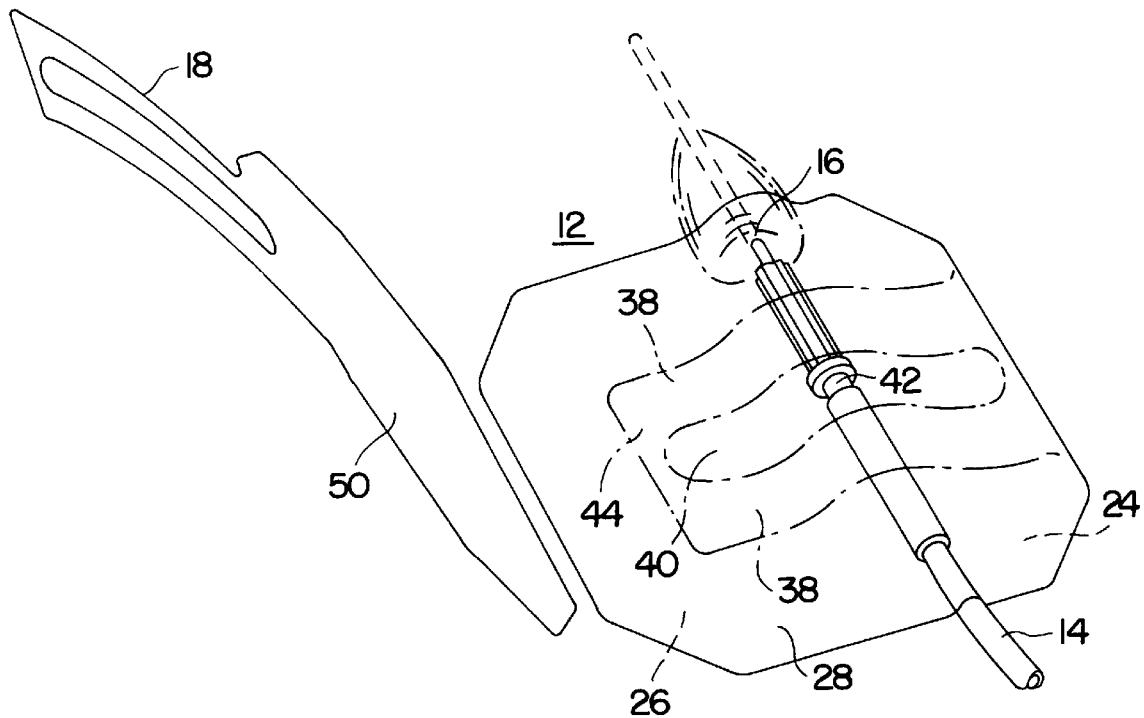

Handle member 18 is then grasped by the operator and rolled or peeled from side 39 of securing member 32, as generally illustrated in FIG. 5b. Handle member 18 is rolled towards larger section 50 thereof generally up to or just beyond hinge section 46. Larger section 50 of handle member 18 is adhered to entry point covering side 26 of cover dressing 24 and the operator then pulls handle member 18 back across medical device 14 which causes cover dressing 24 to fold along hinge section 46 generally over securing member 32 while handle member 18 is simultaneously peeled away from entry point covering side 26 of cover dressing 24, as generally illustrated in FIG. 5c. The operator continues to pull handle member 18 across medical device 14 in relatively close proximity to securing member 32 and completely pulls handle member 18 away from cover dressing 24, as illustrated in FIG. 5d. The operator is careful to ensure that cover dressing 24 completely covers wound site 16. Once handle member 18 is completely peeled away, cover dressing 24 essentially covers and seals the insertion wound 16 and securing member 32 and thereby provides an effective barrier to outside contaminates. The operator then gently presses cover dressing 24 against the patient's skin to ensure that cover dressing 24 bonds to the skin, particularly around the insertion wound.

It should be appreciated by those skilled in the art that various modifications and variations can be made in the present invention without departing from the scope and spirit of the invention. For example, device 10 may comprise any conventional shape or size, and include a number of applications in the medical field. It is intended that the present invention cover such modifications and variations as come within the scope of the appended claims and their equivalents.

What is claimed is:

1. A method of securing a medical device to a patients's skin wherein the medical device is inserted through the patient's skin, said method comprising:

attaching the medical device to the patient's skin adjacent a point of insertion of the medical device through the patient's skin by placing an adhesive securing member over a longitudinally extending portion of said medical device at the point of insertion, the securing member having a cover dressing attached to an end thereof to be folded over the securing member, the longitudinally extending portion disposed directly against the patient's skin at the point of insertion and not sandwiched between the securing member and the subsequently folded over cover dressing;

folding the cover dressing back over the adhesive securing member and pressing the cover dressing against the securing member and the patient's skin adjacent to the securing member;

and covering the point of insertion of the medical device through the patient's skin with the folded over cover dressing to provide a sterile environment for the insertion point wound.

2. The method as in claim 1, comprising folding the cover dressing at a hinge section generally at a connection location of the cover dressing with the securing member.

3. The method as in claim 1, wherein the cover dressing has adhesive on the side thereof covering the insertion wound, said method comprising pressing the adhesive side of the cover dressing against the patient's skin around the insertion wound.

4. The method as in claim 3, wherein a handle member is releasably attached to the adhesive on the cover dressing, said method comprising simultaneously peeling the handle member from the cover dressing while using the handle member to fold the cover dressing back over the securing member so that the side of the cover dressing to be pressed against the patient's skin and over the insertion wound is not touched by the operator.

5. The method as in claim 1, further comprising removing a protective member from the adhesive securing member as a first step prior to securing the medical device to the patient's skin with the securing member.

6. The method as in claim 5, wherein a handle member is releasably attached to an adhesive on a side of the cover dressing to be pressed against the patient's skin, said method comprising simultaneously peeling the handle member from the cover dressing while using the handle member to fold the cover dressing back over the securing member so that the side of the cover dressing to be pressed against the patient's skin and over the insertion wound is not touched by the operator.

7. The method as in claim 1, wherein said method is used to attach a catheter device to the patient's skin.

* * * * *